United States Patent [19]

Furr

[11] 4,089,951

[45] May 16, 1978

[54] OESTRUS OR MENSTRUAL REGULATION

[75] Inventor: Barrington John Albert Furr, Macclesfield, England

[73] Assignee: Imperial Chemical Industries Limited, London, England

[21] Appl. No.: 777,423

[22] Filed: Mar. 14, 1977

[30] Foreign Application Priority Data

Apr. 14, 1976 United Kingdom ............... 15249/76

[51] Int. Cl.$^2$ ................. A61K 31/625; A61K 31/215; A61K 31/19
[52] U.S. Cl. .................................. 424/232; 424/233; 424/234; 424/250; 424/251; 424/258; 424/263; 424/270; 424/273 R; 424/274; 424/275; 424/305; 424/317; 424/319

[58] Field of Search ............... 424/234, 273, 274, 305, 424/317, 250, 251, 258, 263, 270, 275, 319, 232, 233

[56] References Cited

U.S. PATENT DOCUMENTS

| | | | |
|---|---|---|---|
| 3,781,429 | 12/1973 | Partridge et al. ..................... | 424/234 |
| 3,928,588 | 12/1975 | Robert ................................. | 424/234 |
| 3,937,801 | 2/1976 | Lippmann ............................ | 424/234 |

*Primary Examiner*—Sam Rosen
*Attorney, Agent, or Firm*—Cushman, Darby & Cushman

[57] ABSTRACT

The disclosure relates to a method of returning cycling female mammals to the beginning of a new oestrous cycle by administering to them a known prostaglandin synthetase inhibitor, for example indomethacin, and a known luteolytic prostaglandin, for example cloprostenol or fluprostenol, and compositions containing those two components together.

6 Claims, No Drawings

OESTRUS OR MENSTRUAL REGULATION

This invention relates to compositions and methods which are useful in regulating the menstrual or oestrous cycle in mammals.

It is known that in cycling females of many mammalian species, the administration of certain natural prostaglandins and prostaglandin analogues causes a fairly rapid regression of the corpus luteum, resulting in the existing cycle being shortened and the animals returning to the beginning of a new cycle. Such natural prostaglandins and prostaglandin analogues will, for convenience, be referred to as "luteolytic prostaglandins." However, in certain species there is a period, the length of which varies from species to species, at the beginning of the cycle during which the corpus luteum appears to be not susceptible to this action of luteolytic prostaglandins. We have now discovered, and herein lies our invention, a method by which this refractory period, during which the animals are not susceptible to the action of luteolytic prostaglandins, may be shortened, and by which, at other times, the effective luteolytic dose of a luteolytic prostaglandin may be reduced. This invention is therefore clearly of economic benefit in the controlled breeding of livestock, and is useful in the regulation of menstruation.

Thus, according to the invention there is provided a method of returning cycling female mammals to the beginning of a new menstrual or oestrous cycle, which comprises administering to said animals effective amounts of a known prostaglandin synthetase inhibitor and a known luteolytic prostaglandin.

The prostaglandin synthetase inhibitor and the luteolytic prostaglandin may be administered to the animals in the form of a composition containing both, or the two components may be administered separately. If they are administered separately, one may be administered immediately after the other, or the prostaglandin synthetase inhibitor may be administered first, up to 4 hours before the luteolytic prostaglandin.

Suitable known prostaglandin synthetase inhibitors which may be used in the method of the invention are, for example, aspirin, indomethacin, phenylbutazone, mefenamic acid, flufenamic acid, ibuprofen, flurbiprofen, meclofenac, alclofenac, ketoprofen, fenoprofen, naproxen, voltaren, tolmetin, nifluril, flufenisal, sudoxicam, isoxicam, proquazone, or a quinolone alkanoic acid derivative of the formula:-

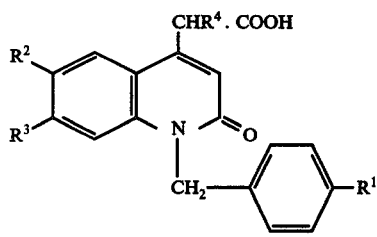

wherein $R^1$ is a hydrogen or chlorine atom, or a methyl, ethyl or trifluoromethyl radical and $R^2$, $R^3$ and $R^4$ are each a hydrogen atom or a methyl radical.

A suitable luteolytic prostaglandin is, for example, prostaglandin $F_2\alpha$, $\omega$-bis-homo-prostaglandin $F_2\alpha$, $9\alpha,11\alpha,15$-trihydroxy-15-methylprosta-4,5,13-trans-trienoic acid, 15-methyl-prostaglandin $F_2\alpha$, 16,16-dimethyl-prostaglandin $F_2\alpha$, 17-phenyl-$\omega$-tetranor-prostaglandin $F_2\alpha$, or a prostaglandin analogue of the formula:

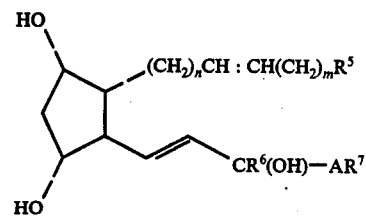

wherein $R^5$ is a carboxy or hydroxymethyl radical or a $C_{2-11}$ alkoxycarbonyl radical, $R^6$ is a hydrogen atom or a $C_{1-4}$ alkyl radical, A is a direct bond or a straight chain $C_{1-3}$ alkylene or alkyleneoxy radical, wherein the oxygen atom is bonded to $R^7$, optionally bearing one or two $C_{1-4}$ alkyl substituents, $n$ is 1 or 2 and $m$ is 2 or 3, and $n$ and $m$ together are 4, and $R^7$ is a phenyl or naphthyl radical optionally bearing one or two substituents selected from halogen atoms, nitro radicals and $C_{1-5}$ alkyl, alkoxy and halogenoalkyl radicals, or a prostaglandin analogue of the formula II wherein $R^5$, $R^6$ and A have the meanings given above, $n$ is 1, $m$ is 3, and $R^7$ is a thiazolyl, indolyl, benzimidazolyl, benzothiazolyl, pyridyl, pyrimidinyl, quinolyl, indolinyl, pyridazinyl, benzo[b]furanyl or benzo[b]thienyl radical optionally substituted by 1 to 4 substituents selected from halogen atoms and $C_{1-3}$ alkyl and alkoxy radicals.

Preferred prostaglandin analogues of the formula II are cloprostenol, fluprostenol and 16-(5-chloropyrid-2-yloxy)-9α,11α,15-trihydroxy-17,18,19,20-tetranor-5-cis,13-transprostadienoic acid.

The prostaglandin synthetase inhibitor and the luteolytic prostaglandin may be administered to animals, by any convenient route but in large animals such as pigs and cattle, intramuscular administration of a substantially aqueous solution is preferred.

The dosage of the two components will, of course, vary depending upon the particular prostaglandin synthetase inhibitor and luteolytic prostaglandin used, but by way of example, a suitable rate of use of a prostaglandin synthetase inhibitor is from 1 to 20mg. per kg. liveweight, and a suitable dose of luteolytic prostaglandin is from 2 to 30μg. per kg. liveweight. As a particular example, a suitable regime for pigs weighing about 150kg. is two 200mg. doses, 4 hours apart, of indomethacin (1.33mg./kg.) and 500 μg. of cloprostenol (3.33μg./kg.).

According to a further feature of the invention there is provided a composition, for use in the method of the invention, which comprises a known prostaglandin synthetase inhibitor and a known luteolytic prostaglandin together with an inert diluent or carrier.

Suitable prostaglandin synthetase inhibitors and luteolytic prostaglandins are those described above.

The composition is preferably in the form of a substantially aqueous solution, which may optionally be buffered, for example with phosphate or citrate, and is preferably sterile. Such a composition may also contain a preservative, and may be made isotonic with sodium chloride. The concentration of the components in such a subtantially aqueous solution is such that the required dosage of each component as defined above is contained in a suitable volume of liquid, preferably between 1 and 10ml.

For use in menstrual regulation, the composition may be in the form of a suppository or pessary containing from 10mg. to 1g. of a prostaglandin synthetase inhibitor and from 50μg. to 5mg. of a luteolytic prostaglandin.

The compositions are manufactured by conventional processes and include conventional excipients.

The invention is illustrated but not limited by the following Examples:

EXAMPLE 1

In a group of six gilts between days 7 and 10 of the oestrous cycle, two were treated with indomethacin (2 × 200mg. 4 hours apart), two were treated with cloprostenol (500μg.) and the other two were treated with indomethacin (2 × 200mg. 4 hours apart) followed by cloprostenol (500μg.). Neither the animals treated with indomethacin alone, nor the animals treated with cloprostenol alone showed a premature return to oestrus, but luteolysis occured in both animals treated with indomethacin and cloprostenol, and they returned to oestrus three to four days after the treatment.

EXAMPLE 2

Groups of hysterectomised guinea pigs were treated on the morning of the 19th and 20th days of the extended cycle as shown in the left hand column of the table below, and the number of animals returning to oestrus, as indicated by vaginal opening, is shown in the right hand column. It can be seen that 2 × 5μg. of fluprostenol and 2 × 20mg. of indomethacin are each ineffective, whereas if the two compounds are given together, a high rate of luteolysis, indicated by vaginal opening, is achieved.

| Treatment given on Days 19 & 20 | Number showing vaginal opening/number in group |
|---|---|
| Indomethacin (20mg.) | 0/5 |
| Fluprostenol (200 μg.) | 5/5 |
| Fluprostenol (100μg.) | 10/10 |
| Fluprostenol (50μg.) | 5/5 |
| Fluprostenol (15μg.) | 3/5 |
| Fluprostenol (5μg.) | 1/5 |
| Indomethacin (20mg.) + fluprostenol (5μg.) 90 minutes later | 4/5 |
| Indomethacin (20mg.) + fluprostenol (5μg.) 180 minutes later | 4/5 |

EXAMPLE 3

Regularly cycling gilts were treated between days 6 and 10 of the oestrous cycle with either:
1. — 200mg. of indomethacin intramuscularly at 10.00 and 14.00 hours;
2. — 500μg. of cloprostenol intramuscularly at 14.00 hours; or
3. — 200mg. of indomethacin intramuscularly at 10.00 and 14.00 hours followed by 500μg. of cloprostenol intramuscularly at 14.00 hours.

and the following results were obtained:

| Treatment | No. of animals treated | No. of animals showing premature oestrus. |
|---|---|---|
| 1 | 8 | 2 |
| 2 | 7 | 2 |
| 3 | 9 | 6 |

EXAMPLE 4

Normally cycling female guinea pigs were hysterectomised on Day 6 of the cycle and then treated with a single subcutaneous dose of fluprostenol on each of Days 19 and 20 of the extended cycle (vaginal opening would normally be evident around Day 15 in intact animals). The animals were then inspected daily during the next 8 days for signs of vaginal opening.

Dose-related responses were seen with doses between 5 and 50μg./animal, the latter being the smallest dose which elicited vaginal opening in all the animals treated.

In a second series of experiments, indomethacin (20mg./kg. subcutaneously) was given 3 hours prior to the administration of fluprostenol, again on each of Days 19 and 20 of the cycle extended by hysterectomy. In these experiments dose-related responses were seen with doses of fluprostenol of 2.5 to 12.5μg./animal, the latter causing vaginal opening in all the animals treated.

None of a group of guinea pigs given indomethacin (20mg./kg.) alone exhibited vaginal opening during 8 days after treatment.

Thus, when given in combination with indomethacin (2 × 200mg./kg.), fluprostenol is fully effective at a dose level of 12.5μg./animal, whereas with fluprostenol alone, about four time this dose level, 50μg./animal, is required to produce a similar luteolytic effect.

What we claim is:

1. A method of returning cycling female mammals to the beginning of a new menstrual or oestrus cycle, during the period at the beginning of the cycle when the corpus luteum is not susceptible to the action of a luteolytic prostaglandin which comprises administering to said animals an effective amount of a known prostaglandin synthetase inhibitor and a known luteolytic prostaglandin.

2. The method of claim 1 wherein the prostaglandin synthetase inhibitor and the luteolytic prostaglandin are administered to the animals in the form of a composition containing both.

3. The method of claim 1 wherein the prostaglandin synthetase inhibitor is aspirin, indomethacin, phenylbutazone, mefenamic acid, flufenamic acid, ibuprofen, flurbiprofen, meclofenac, alclofenac, ketoprofen, naproxen, voltaren, tolmetin, nifluril, flufenisal, sudoxicam, isoxicam, proquazone or a quinolone alkanoic acid derivative of the formula:

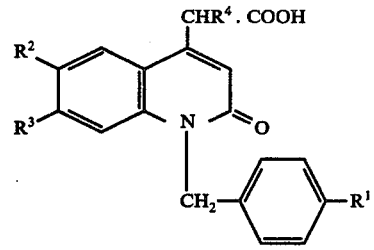

wherein $R^1$ is a hydrogen or chlorine atom or a methyl, ethyl or trifluoromethyl radical, and $R^2$, $R^3$, and $R^4$ are each a hydrogen atom or a methyl radical.

4. The method of claim 1 wherein the luteolytic prostaglandin is prostaglandin $F_2\alpha$,ω-bis-homo-prostaglandin $F_2\alpha$, 9α,11α,15-trihydroxy-15-methylprosta-4,5,13-trans-trienoic acid, 15-methyl-prostaglandin $F_2\alpha$, 16,16-dimethyl-prostaglandin $F_2\alpha$, 17-phenyl-ω-tetranorprostaglandin $F_2\alpha$, or a prostaglandin analogue of the formula:

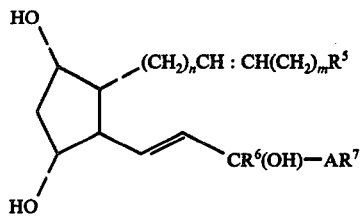

wherein $R^5$ is a carboxy or hydroxymethyl radical or a $C_{2-11}$ alkoxycarbonyl radical, $R^6$ is a hydrogen atom or a $C_{1-4}$-alkyl radical, A is a direct bond or a straight chain $C_{1-3}$-alkylene or alkyleneoxy radical, wherein the oxygen atom is bonded to $R^7$, optionally bearing one or two $C_{1-4}$-alkyl substituents, $n$ is 1 or 2 and $m$ is 2 or 3, and $n$ and $m$ together are 4, and $R^7$ is a phenyl or naphthyl radical optionally bearing one or two substituents selected from halogen atoms, nitro radicals and $C_{1-5}$-alkyl, alkoxy and halogenoalkyl radicals, or a prostaglandin analogue of the formula II wherein $R^5$, $R^6$ and A have the meanings given above, $n$ is 1, $m$ is 3, and $R^7$ is a thiazolyl, indolyl, benzimidazolyl, benzothiazolyl, pyridyl, pyrimidinyl, quinolyl, indolinyl, pyridazinyl, benzo[b]furanyl or benzo[b]thienyl radical optionally substituted by 1 to 4 substituents selected from halogen atoms and $C_{1-3}$-alkyl and alkoxy radicals.

5. The method of claim 4 wherein the luteolytic prostaglandin analogue is cloprostenol, fluprostenol or 16-(5-chloropyrid-2-yloxy)-9α,11α,15-trihydroxy-17,18,19,20-tetranor-5-cis,13-trans-prostadienoic acid.

6. The method of claim 1 which comprises the administration to the animals of from 1 to 20mg. per kg. liveweight of the prostaglandin synthetase inhibitor and from 2 to 30μg. per kg. liveweight of a luteolytic prostaglandin.

* * * * *